United States Patent
VanVelzen et al.

(10) Patent No.: US 9,658,204 B2
(45) Date of Patent: May 23, 2017

(54) STOICHIOMETRIC AIR TO FUEL RATIO SENSOR SYSTEM

(71) Applicant: Continental Automotive Systems, Inc., Auburn Hills, MI (US)

(72) Inventors: Isaac P. VanVelzen, Clarkston, MI (US); Brian J. McKay, West Bloomfield, MI (US)

(73) Assignee: Continental Automotive Systems, Inc., Auburn Hills, MI (US)

( * ) Notice: Subject to any disclaimer, the term of this patent is extended or adjusted under 35 U.S.C. 154(b) by 254 days.

(21) Appl. No.: 14/289,688

(22) Filed: May 29, 2014

(65) Prior Publication Data

US 2015/0323481 A1 Nov. 12, 2015

Related U.S. Application Data

(60) Provisional application No. 61/990,263, filed on May 8, 2014.

(51) Int. Cl.
*G01N 33/28* (2006.01)
*F02D 41/00* (2006.01)
(Continued)

(52) U.S. Cl.
CPC ....... *G01N 33/2852* (2013.01); *F02D 19/084* (2013.01); *F02D 19/087* (2013.01);
(Continued)

(58) Field of Classification Search
CPC .. G01N 27/226; G01N 27/12; G01N 33/2852; H01M 8/04194; F02D 19/084;
(Continued)

(56) References Cited

U.S. PATENT DOCUMENTS 4,824,549 A * 4/1989 Hamada ............... G01N 27/417
204/410
4,905,655 A * 3/1990 Maekawa ........... F02D 19/0684
123/1 A (Continued)

OTHER PUBLICATIONS

Chiang, Michael, et al. "Estimation of the Stoichiometric Air-Fuel Ratio in Liquefied Petroleum Gas-Injected Engines." SAE Paper (2002): 01-2738.*

(Continued)

*Primary Examiner* — Lisa Caputo
*Assistant Examiner* — Punam Roy

(57) ABSTRACT

A sensor system (36) determines the Stoichiometric Air to Fuel Ratio (SAFR) of fuel mixtures. The system includes a first electrode (12) and a second electrode (14), with the first electrode surrounding the second electrode so that a fuel mixture can flow between the first electrode and the second electrode. The electrodes are constructed and arranged to provide data for determining a conductivity and permittivity of the fuel mixture. A temperature sensor (18) is constructed and arranged to measure a temperature of the fuel mixture. A processor (19) is constructed and arranged to determine the SAFR of the fuel mixture based on the measured temperature and permittivity of the fuel mixture.

6 Claims, 3 Drawing Sheets

(51) Int. Cl.
*F02D 19/08* (2006.01)
*G01N 27/22* (2006.01)
*G01K 13/02* (2006.01)

(52) U.S. Cl.
CPC ....... *F02D 41/0002* (2013.01); *G01N 27/226* (2013.01); *F02D 2200/0611* (2013.01); *G01K 13/02* (2013.01)

(58) Field of Classification Search
CPC ............... F02D 19/087; F02D 19/0634; F02D 2200/0611; F02D 41/0025; F02D 41/0002; F02D 41/2454; G01K 13/02
See application file for complete search history.

(56) References Cited

U.S. PATENT DOCUMENTS

| | | | | |
|---|---|---|---|---|
| 4,915,084 | A * | 4/1990 | Gonze | F02B 11/00 |
| | | | | 123/1 A |
| 4,945,863 | A * | 8/1990 | Schmitz | G01N 33/2852 |
| | | | | 123/1 A |
| 4,971,015 | A * | 11/1990 | Gonze | F02B 11/00 |
| | | | | 123/478 |
| 4,981,125 | A * | 1/1991 | Kato | G01N 27/417 |
| | | | | 123/693 |
| 5,060,619 | A * | 10/1991 | Sakurai | F02D 19/0628 |
| | | | | 123/1 A |
| 5,134,381 | A * | 7/1992 | Schmitz | G01N 33/2852 |
| | | | | 324/663 |
| 5,367,264 | A * | 11/1994 | Brabetz | G01R 27/2605 |
| | | | | 324/663 |
| 5,543,722 | A * | 8/1996 | Suzuki | G01N 33/2852 |
| | | | | 324/663 |
| 5,592,098 | A * | 1/1997 | Suzuki | G01N 33/2852 |
| | | | | 324/663 |
| 6,566,892 | B2 * | 5/2003 | Schaefer | G01N 33/2852 |
| | | | | 324/601 |
| 6,586,123 | B1 * | 7/2003 | Yi | H01M 8/04089 |
| | | | | 429/431 |
| 6,842,017 | B2 | 1/2005 | McKenzie et al. | |
| 6,927,583 | B2 * | 8/2005 | Vanzuilen | G01N 27/226 |
| | | | | 324/686 |
| 8,274,298 | B2 * | 9/2012 | Woods | G01N 27/228 |
| | | | | 324/601 |
| 8,640,681 | B2 * | 2/2014 | Kawai | F02D 41/0002 |
| | | | | 123/575 |
| 9,097,696 | B2 * | 8/2015 | Kassner | G01N 33/2847 |
| 2004/0004487 | A1 * | 1/2004 | Vanzuilen | G01N 27/226 |
| | | | | 324/663 |
| 2004/0195531 | A1 * | 10/2004 | Rahmouni | G01N 33/225 |
| | | | | 250/573 |
| 2010/0007360 | A1 * | 1/2010 | Kaess | G01N 33/2852 |
| | | | | 324/672 |
| 2010/0225334 | A1 * | 9/2010 | Uchida | G01N 33/2852 |
| | | | | 324/663 |
| 2013/0342223 | A1 * | 12/2013 | Kato | G01N 27/22 |
| | | | | 324/663 |

OTHER PUBLICATIONS

Takeuchi, K., et al. "A capacitance sensor for methanol ratio measurement of blended gasoline." Automotive Electronics, 1991, Eighth International Conference on. IET, 1991.*

"Flex Fuel Sensors". The Clemson University Vehicular Electronics Laboratory. 2 pages. Apr. 6, 2012. Accessed online on Mar. 31, 2016 at <https://web.archive.org/web/20120406140918/http://www.cvel.clemson.edu/auto/sensors/flex-fuel-sensor.html>.*

Rocha, Marcelo da Silva, and J. R. Simões-Moreira. "A simple impedance method for determining ethanol and regular gasoline mixtures mass contents." Fuel 84.4 (2005): 447-452.*

Pikūnas, Alvydas, Saugirdas Pukalskas, and Juozas Grabys. "Influence of Composition of Gasoline-Ethanol Blends on Parameters of Internal Combustion Engines." Journal of KONES Internal Combustion Engines 10 (2003): 3-4.*

Bayraktar, Hakan. "Experimental and theoretical investigation of using gasoline-ethanol blends in spark-ignition engines." Renewable Energy 30.11 (2005): 1733-1747.*

K. h. Ahn, A. G. Stefanopoulou and M. Jankovic, "AFR-Based Fuel Ethanol Content Estimation in Flex-Fuel Engines Tolerant to MAF Sensor Drifts," in IEEE Transactions on Control Systems Technology, vol. 21, No. 3, pp. 590-603, Apr. 3, 2012.*

Bayraktar, Hakan. "Theoretical investigation of flame propagation process in an SI engine running on gasoline-ethanol blends." Renewable Energy 32.5 (2007): 758-771.*

Schmitz, Günter, et al. Intelligent alcohol fuel sensor. No. 900231. SAE Technical Paper, 1990.*

Turner, James WG, et al. GEM ternary blends: testing iso-stoichiometric mixtures of gasoline, ethanol and methanol in a production flex-fuel vehicle fitted with a physical alcohol sensor. No. 2012-01-1279. SAE Technical Paper, 2012.*

Air Fuel Ratio comparison. 2006. Giles Desomeaux. Accessed online at <http://ethanolpro.tripod.com/id213.html>.*

* cited by examiner

| Gasoline | Ethanol | Methanol | Expected SAFR | Expected Dielectric |
|---|---|---|---|---|
| 100 | 0 | 0 | 14.7 | 2.0 |
| 90 | 0 | 10 | 13.9 | 5.1 |
| 80 | 20 | 0 | 13.6 | 6.5 |
| 80 | 10 | 10 | 13.3 | 7.3 |
| 60 | 20 | 20 | 11.9 | 12.7 |
| 60 | 10 | 30 | 11.7 | 13.6 |
| 60 | 30 | 10 | 12.2 | 11.8 |
| 50 | 25 | 25 | 11.2 | 15.4 |
| 40 | 30 | 30 | 10.5 | 18.0 |
| 40 | 40 | 20 | 10.8 | 17.1 |
| 40 | 20 | 40 | 10.3 | 18.9 |
| 34 | 33 | 33 | 10.1 | 19.6 |
| 20 | 40 | 40 | 9.1 | 23.4 |
| 20 | 20 | 60 | 8.6 | 25.1 |
| 20 | 60 | 20 | 9.6 | 21.6 |
| 10 | 45 | 45 | 8.4 | 26.0 |
| 10 | 70 | 20 | 9.1 | 23.8 |
| 10 | 20 | 70 | 7.8 | 28.2 |
| 15 | 85 | 0 | 9.9 | 21.0 |
| 15 | 0 | 85 | 7.7 | 28.4 |
| 0 | 100 | 0 | 9.0 | 24.3 |
| 0 | 0 | 100 | 6.5 | 33.1 |

Permittivity and SAFR of Various Fuel Blends

STOICHIOMETRIC AIR TO FUEL RATIO SENSOR SYSTEM

FIELD

The embodiment relates to a stoichiometric air to fuel ratio (SAFR) sensor system for measuring the permittivity, conductivity and temperature of a given fuel mixture and for outputting the SAFR.

BACKGROUND

The use of alcohols as alternative fuel is becoming more and more prevalent. One of the biggest challenges to using alcohols as fuel is the difference in the Stoichiometric Air to Fuel Ratio (SAFR) of gasoline to that of alcohols. The differing SAFRs means that the fuel pump and fuel injectors must supply a different volume of fuel depending on the concentration of alcohol in the fuel. This challenge is further exacerbated by the fact the different types of alcohols have different SAFRs.

A conventional flex fuel sensor is able to determine the concentration of ethanol in a given fuel, or alternately, the concentration of methanol in a given fuel. The shortcoming of this technology is that it cannot measure both. Each sensor must be calibrated for either ethanol or methanol, and will be inaccurate if the other is present in the fuel. This limitation in measurement flexibility would cause problems in a market that offers both alternative fuels.

An alternate conventional solution employs a wide range oxygen sensor, also known as a Lambda sensor. This method employs an oxygen sensor in the exhaust line to measure the amount of oxygen remaining after combustion. The fuel to air ratio is then adjusted accordingly. This is a feedback method and can only make adjustments after combustion has already taken place. A refueling event can cause a large shift in the alcohol content, which can take several minutes for the Lambda sensor to detect. This delay results in excess emissions and loss of performance of the vehicle, while the system "learns" the properties of the new fuel.

A conventional near infrared sensor can eliminate the concentration of gasoline, methanol, and ethanol blends with good accuracy. However, the cost of the near infrared sensor is high, and the sensor can suffer from environmental and durability limitations.

Thus, there is a need to provide a sensor system for measuring the permittivity, conductivity and temperature of a given fuel and for outputting the SAFR so as to be fed forward to an engine control module.

SUMMARY

An object of the present invention is to fulfill the need referred to above. In accordance with the principles of an embodiment, this objective is obtained by a sensor system that determines the Stoichiometric Air to Fuel Ratio (SAFR) of fuel mixtures. The system includes a first electrode and a second electrode, with the first electrode surrounding the second electrode so that a fuel mixture can flow between the first electrode and the second electrode. The electrodes are constructed and arranged to provide data for determining a conductivity and permittivity of the fuel mixture. A temperature sensor is constructed and arranged to measure a temperature of the fuel mixture. A processor is constructed and arranged to determine the SAFR of the fuel mixture based on the measured temperature and permittivity of the fuel mixture.

In accordance with another aspect of the embodiment, a method is provided for determining Stoichiometric Air to Fuel Ratio (SAFR) of fuel mixtures. The method measures a conductivity of a fuel mixture, determines a permittivity of the fuel mixture, and measures a temperature of the fuel mixture. Based on the determined permittivity and temperature of the fuel mixture, the SAFR of the fuel mixture is determined, which can be fed-forward to an engine control module.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

BRIEF DESCRIPTION OF THE DRAWINGS

The invention will be better understood from the following detailed description of the preferred embodiments thereof, taken in conjunction with the accompanying drawings, wherein like reference numerals refer to like parts, in which.

DETAILED DESCRIPTION OF AN EXAMPLE EMBODIMENT

Figures 1, 2:
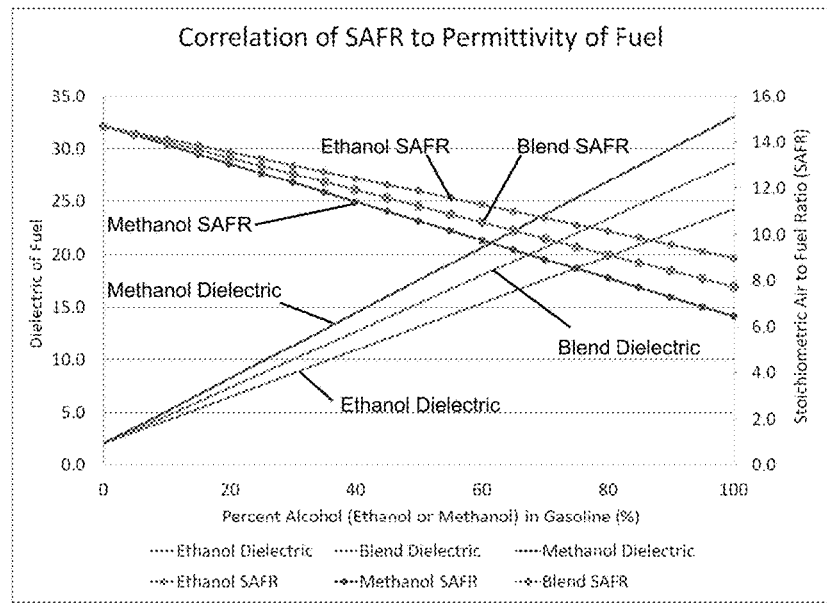
FIG. 1 is a graph showing the correlation of SAFR to permittivity of fuel.
FIG. 2 is a table showing the permittivity and SAFR of various fuel blends.

In accordance with the embodiment discussed below, it has been determined that the Stoichiometric Air to Fuel Ratio (SAFR) of a given fuel can be correlated to its dielectric properties, independent of the type of alcohol being used. The correlation of dielectric properties to SAFR is shown in FIG. 1. As shown, as the concentration of alcohol in the fuel increases along the X axis the permittivity increases, and the SAFR decreases. The table of FIG. 2 shows the permittivity and SAFR of various fuel blends.

Figure 3:
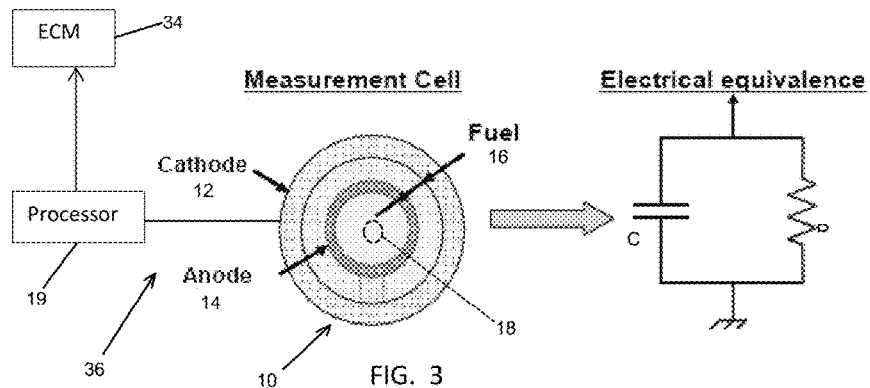
FIG. 3 is a schematic view of a measurement cell and its electrical equivalent in accordance with an embodiment.

With reference to FIG. 3, a measurement cell, generally indicated at 10, provided in accordance with an embodiment, obtained the data of FIGS. 1 and 2. The measurement cell 10 has a first sensor electrode 12 that is a cathode, and a second sensor electrode 14 that is an anode. The electrodes define a capacitor. The electrical equivalence of the measurement cell 10 is also shown in FIG. 3, where the capacitor C is in parallel with a resistor R. The first electrode 12 surrounds the second electrode 14. A fuel mixture 16 flows between the electrodes 12 and 14 so that the electrodes can provide data for determining the conductivity and permittivity of the fuel mixture 16. The capacitor C effectively operates in two different modes (using two different oscillators for example) so that the permittivity and conductivity measurements can be made. Since the permittivity of each fuel varies as a function of temperature, the temperature of the fuel must also be known to accurately determine the SAFR, as explained below. Thus, the cell 10 includes a temperature sensor 18, such as a thermistor. A processor 19 is associated with the measurement cell 10 and is constructed and arranged to perform desired calculations and to output desired results. The measurement cell 10 and processor 19 define a sensor system 36 of the embodiment. It can be appreciated that the processor can be part of the cell 10.

The measurement cell 10 can be of the type described in U.S. Pat. No. 6,842,017 B2, the content of which is hereby incorporated by reference into this specification. This conventional sensor measures the permittivity, conductivity, and temperature of a given fuel and outputs the ethanol or methanol concentration.

Figure 4:
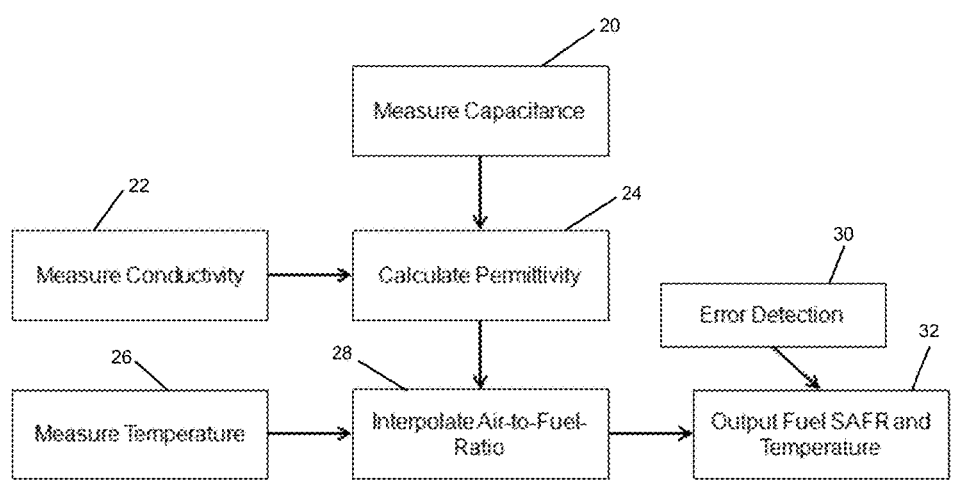
FIG. 4 is a flow diagram of a measurement principle obtained by the measurement cell and processor of FIG. 3.

FIG. 4 is a flow diagram of the measurement principle in accordance with an embodiment, using the measurement cell 10 of FIG. 3. In step 20, a capacitance of the fuel mixture 16 is measured. In step 22, the conductivity of the fuel mixture 16 is measured and in step 24, based on the measured capacitance and conductivity, the permittivity of the fuel 16 is calculated by processor 19. The temperature of the fuel 16 is measured by the temperature sensor 18 in step 26. Based on the measured temperature and permittivity, the air-to-fuel ratio of the fuel 16 is interpolated by the processor 19 in step 28. Error detection is performed in step 30 and in step 32, the fuel SAFR and temperature are outputted from the processor 19 to an engine control module (ECM) 34 (FIG. 3).

Thus, instead of outputting the conventional ethanol or methanol concentration of the fuel 16, the measurement cell 10 and processor 19 determine the permittivity, conductivity, and temperature of a given fuel and the processor outputs the SAFR. The software in processor 19 is configured to measure blends of gasoline, methanol and ethanol. The conventional sensor noted above is restricted to blends of gasoline and methanol or gasoline and ethanol since the addition of alcohol causes errors with the conventional software.

Figure 5:
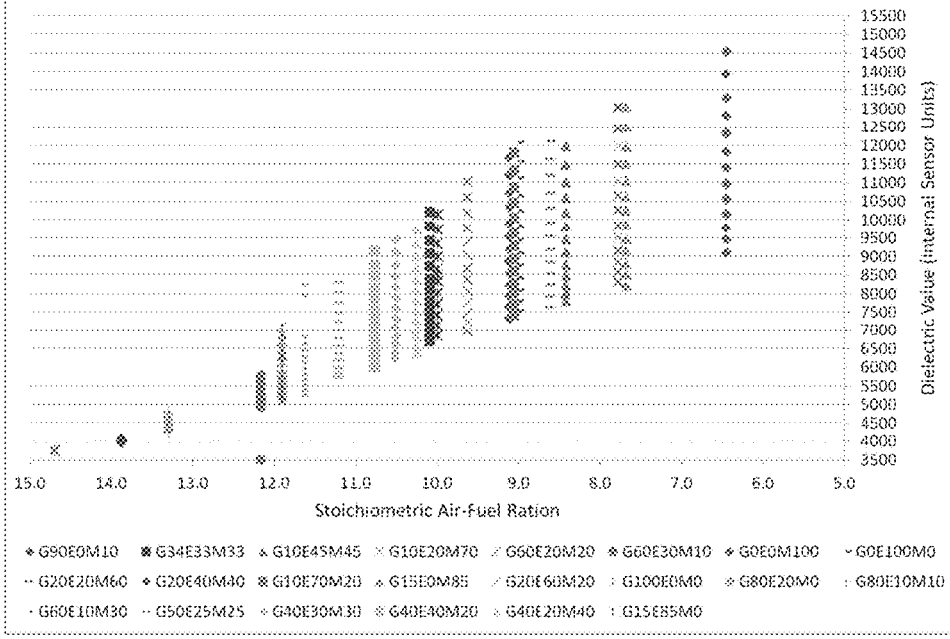
FIG. 5 is graph showing SAFR vs. dielectric value for a first test sample.
Figure 6:
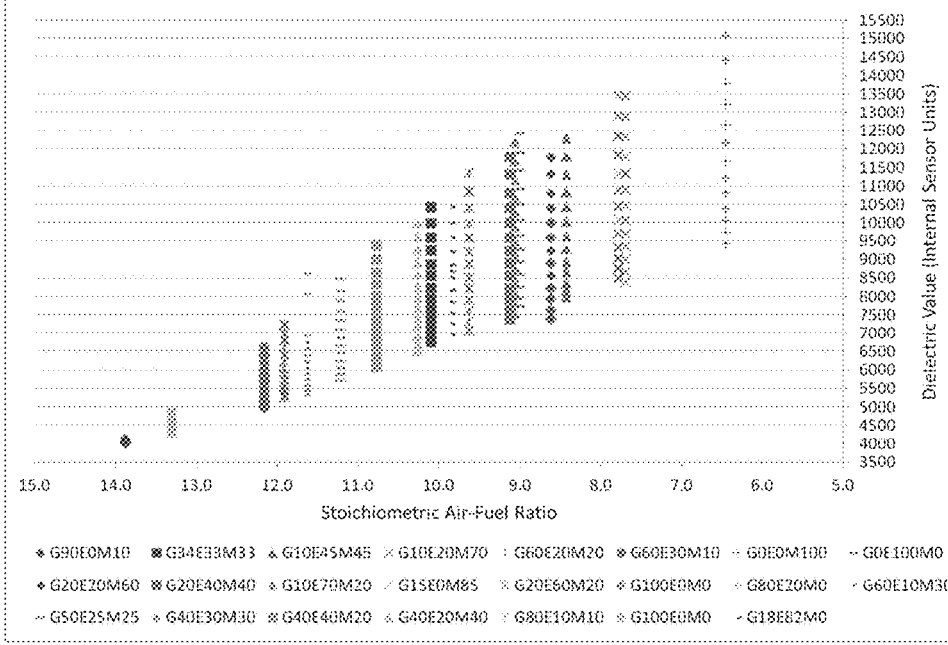
FIG. 6 is graph showing SAFR vs. dielectric value for a second test sample.

Testing confirmed that there is a correlation between the dielectric value of a fuel and the air-to-fuel ratio of that fuel. Furthermore, the dielectric value can be mapped with a high degree of accuracy to the air-to-fuel ratio required for a stoichiometric burn of that fuel in an internal combustion engine, regardless of the actual composition of that fuel. The graphs in FIGS. 5 and 6, regarding two different test samples, show the relationship of permittivity and SAFR over the temperature range of −40° C. to 125° C. Each set of data marks represents one fuel blend over the temperature range, with SAFR shown along the X axis and permittivity shown along the Y axis.

Thus, measuring the dielectric of a fuel flowing through the measurement cell 10, the SAFR can be determined which is useful for fuel injection and cold start strategies for a combustion engine. The SAFR value can then be "fed forward" to the engine control module 34 to adjust the SAFR prior to combustion, in order to minimize emissions and maximize performance. This feed-forward control scheme addresses the shortcomings of the conventional Lambda sensor or near infrared sensor mentioned above. The feed-forward approach will improve engine combustion efficiency, reduce pollutant emissions, and prevent mechanical issues such as engine knocking and backfire which may occur with a conventional oxygen (Lambda) sensor.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A sensor system for determining Stoichiometric Air to Fuel Ratio (SAFR) of fuel mixtures, the system comprising:
   a first electrode,
   a second electrode, with the first electrode surrounding the second electrode so that a fuel mixture can flow between the first electrode and the second electrode, the electrodes being constructed and arranged to provide data for determining a conductivity and permittivity of the fuel mixture,
   a temperature sensor constructed and arranged to measure a temperature of the fuel mixture, and
   a processor constructed and arranged to determine the SAFR of the fuel mixture based on the measured temperature and permittivity of the fuel mixture,
   wherein the fuel mixture comprises blends of gasoline, methanol and ethanol, and
   wherein the sensor system is in combination with an engine control module of an internal combustion engine, wherein the SAFR is fed from the processor forward to the engine control module so as to adjust the SAFR prior to combustion.

2. The system of claim 1, wherein the first electrode defines a cathode and the second electrode defines an anode.

3. A method of determining the Stoichiometric Air to Fuel Ratio (SAFR) of fuel mixtures, the method comprising the steps of:
   measuring a conductivity of a fuel mixture,
   determining a permittivity of the fuel mixture,
   measuring the temperature of the fuel mixture,
   based on the determined permittivity and temperature of the fuel mixture, determining the SAFR of the fuel mixture,
   feeding the determined SAFR of the fuel mixture forward to an engine control module of an internal combustion engine, and
   adjusting the SAFR prior to combustion,
   wherein the fuel mixture comprises blends of gasoline, methanol and ethanol.

4. The method of claim 3, wherein the step of measuring conductivity comprises using a first electrode and a second electrode, with the first electrode surrounding the second electrode so that the fuel mixture can flow between the first electrode.

5. The method of claim 4, wherein the first electrode defines a cathode and the second electrode defines an anode, the method including determining a capacitance of the fuel mixture.

6. The method of claim 5, wherein the step of calculating permittivity includes using the determined capacitance and the measured conductivity of the fuel mixture.

* * * * *